US008248072B1

United States Patent
Colson et al.

(10) Patent No.: US 8,248,072 B1
(45) Date of Patent: Aug. 21, 2012

(54) METHOD AND APPARATUS FOR AUTOMATED RAW MATERIAL SCREENING

(75) Inventors: Kimberly L. Colson, Westford, MA (US); Joshua M. Hicks, Billerica, MA (US); Christian Fischer, Rheinstetten (DE)

(73) Assignee: Bruker Biospin Corporation, Billerica, MA (US)

( * ) Notice: Subject to any disclaimer, the term of this patent is extended or adjusted under 35 U.S.C. 154(b) by 39 days.

(21) Appl. No.: 13/082,006

(22) Filed: Apr. 7, 2011

(51) Int. Cl.
*G01V 3/00* (2006.01)
(52) U.S. Cl. ........................................ 324/312; 324/309
(58) Field of Classification Search ................. 324/312, 324/309, 307, 300
See application file for complete search history.

(56) References Cited

U.S. PATENT DOCUMENTS

| | | | | |
|---|---|---|---|---|
| 6,683,455 B2 * | 1/2004 | Ebbels et al. | ................. | 324/309 |
| 7,181,348 B2 * | 2/2007 | Wishart et al. | ................. | 702/22 |
| 7,457,708 B2 * | 11/2008 | Thompson et al. | ............ | 702/19 |
| 7,493,225 B2 * | 2/2009 | Wang et al. | ..................... | 702/85 |

OTHER PUBLICATIONS

"Use of the DPX400 Via IconNMR", HVR:Documents:Equipment Instructions:dpx400:IconNMR, Apr. 14, 2009, 2 pages.

* cited by examiner

*Primary Examiner* — Louis Arana
(74) *Attorney, Agent, or Firm* — Law Offices of Paul E. Kudirka

(57) ABSTRACT

An automated screening device that performs standardized system suitability tests and evaluations and measures components of a submitted sample to assist in the quality control screening of raw materials, ingredients, pharmaceuticals, chemicals, polymers, food products, petroleum and many other materials. After determining the performance suitability of an NMR spectrometer, the system permits samples to be submitted for screening. An NMR spectrum of a sample is acquired and a qualitative analysis unit identifies at least one reference NMR spectrum corresponding a compound present in the sample and a quantitative analysis unit integrates relative signal intensity signals of the sample spectrum in regions of peak intensity in the one reference NMR spectrum and compares integration results to a number of atoms in each region in order to confirm identification of the compound.

28 Claims, 6 Drawing Sheets

METHOD AND APPARATUS FOR AUTOMATED RAW MATERIAL SCREENING

BACKGROUND

Nuclear magnetic resonance (NMR) is a physical phenomenon involving quantum mechanical magnetic properties of atomic nuclei in the presence of an applied, external magnetic field. NMR phenomena can be observed with an NMR spectrometer and used to study molecular physics, crystalline and non-crystalline materials. In particular, nuclear spin phenomena can be used to generate a spectrum comprised of a pattern of lines representing the various spins and spin interactions.

In order to perform an NMR measurement, the instrument must be set up to perform a particular measurement. A sample to be measured must be prepared, inserted into the instrument and a measurement run. The resulting intensity signals must then be processed to generate a spectrum. Finally, the spectrum must be interpreted in order to determine the composition of the sample.

Conventional automation software can be used to control the NMR spectrometer to perform routine measurements and signal processing software is available to process the intensity signals in order to generate an NMR spectrum. However, in order to produce accurate results, the spectrometer must be checked and calibrated. Further, the interpretation of the NMR spectrum is complex process requiring training and experience and a thorough knowledge of the compounds that may be present in the sample. For example, the NMR spectrum may include intensity signals from one or more compounds of interest, the solvent used to dissolve the sample and impurities in the sample and solvent. Consequently, NMR spectrometers are generally maintained and operated by highly trained laboratory scientists known as NMR spectroscopists.

In many production facilities, it would be desirable to make NMR measurements routinely on samples, such as raw materials without having NMR spectroscopists on staff. Often these measurements are simple pass fail measurements. Nonetheless such measurements made on conventional NMR spectrometers still require the training and knowledge of an NMR spectroscopist to perform the measurement and interpret the result.

SUMMARY

In accordance with the principles of the invention, an automated screening device performs standardized NMR measurements on a sample to assist in the quality control screening of raw materials, ingredients and components used in a wide range of products, such as pharmaceuticals, chemicals, polymers, food products, petroleum and many other materials. After acquiring an NMR spectrum of the sample, a qualitative analysis unit identifies at least one reference NMR spectrum corresponding a compound present in the sample and a quantitative analysis unit integrates relative signal intensity signals of the sample spectrum in regions of peak intensity in the one reference NMR spectrum and compares integration results to a number of atoms in each region in order to confirm identification of the compound. The device performs the testing and detection of any compounds having NMR active nuclei using standard NMR techniques, but because it is highly automated, the device can be operated by non-NMR spectroscopists and the measurements performed on NMR spectrometers in good laboratory practice (GLP) environments.

In one embodiment, a qualitative and a quantitative analysis of a sample NMR spectrum are performed in order to initially identify and then confirm identification of various compounds expected in the sample, including a main component, adulterants, impurities and other compounds. A further quantitative analysis is then used to determine the relative amounts of each compound present.

In another embodiment, both the qualitative and the quantitative analysis use data that has been previously stored in databases.

In still another embodiment, the qualitative analysis is performed by comparing the sample NMR spectrum to a plurality of reference spectra stored in a spectral database.

In yet another embodiment, the quantitative analysis is performed by integrating signal intensities in selected regions of the sample spectrum and comparing the integration results to the number of atoms in each region.

In still another embodiment, in order to assure that the NMR spectrometer is performing to user-defined specifications, a series of system suitability tests are periodically run by the raw material screening software.

In yet another embodiment, reports designed for both non-technical and advanced users are automatically generated to allow quick assessment of the results and to provide a permanent record of the material testing.

DETAILED DESCRIPTION

Figure 1:
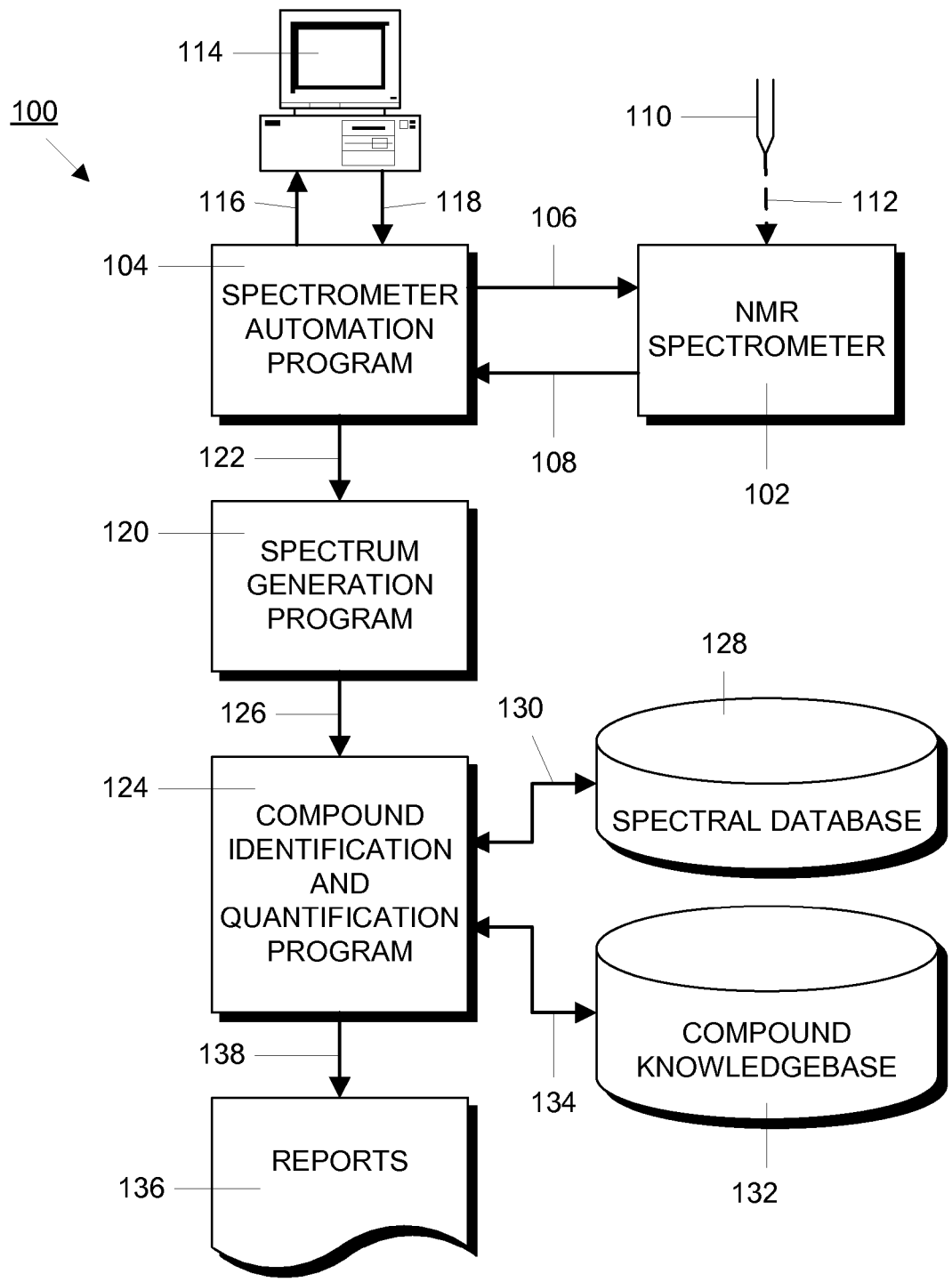
FIG. 1 is a block schematic diagram of a raw material screening system constructed in accordance with the principles of the invention.

FIG. 1 illustrates the basic components of a material analysis system 100 constructed in accordance with the principles of the invention. The NMR spectrometer 102 is controlled by a conventional spectrometer automation program 104 which provides commands to the spectrometer 102 as indicated schematically by arrow 106 and receives information back as indicated schematically by arrow 108. The spectrometer automation program handles a variety of tasks for setting up, running, and processing a routine NMR experiment on the NMR spectrometer 102. These tasks include prompting a user for insertion of a sample 110 as indicated schematically by arrow 112, prompting a user for data file name, solvent, and type of experiment from computer 114 as indicated schematically by arrow 116 and receiving the response as indicated by arrow 118. Since the magnets used in the spectrometer are not perfect and are prone to drift, the automation software locks the spectrometer on the solvent by performing an NMR measurement on a predetermined reference atom (usually deuterium) in the solvent in which the sample 110 is dissolved. The resulting reference signal is used to shim the spectrometer magnet in order to make the magnetic field as uniform as possible. In one embodiment, the system uses the half width of the reference signal to determine if the spectrum is of a high enough quality to be passed on for spectral evaluation. The threshold cutoff for half height is user-selectable. A sample with a larger half width will be re-shimmed and re-acquired. Two consecutive sample failures result in automatic queuing of a System Suitability Test to check the calibration of the spectrometer as described in detail below.

Finally, the spectrometer automation software runs the experiment and acquires the intensity signal (called a free induction decay or FID) over time from the sample 110. A spectrometer automation program which is suitable for use with the invention is sold under the name IconNMR® by the assignee of the present invention.

The FID signal acquired by the spectrometer 102 under control of the automation program 104 is provided to the spectrum generation program 120 as indicated schematically by arrow 122. The spectrum generation program 120 processes the FID signal by Fourier transformation and does phasing to correct for phase shifts in the frequency components of the FID signal. In one embodiment, the program 120 integrates $^1$H spectra, performs peak selection (peak-picking) and finally plots the spectrum as a table of values. A spectrum generation program suitable for use with the present invention is sold under the name TopSpin® by the assignee of the present invention. Alternatively, $^{13}$C, $^{19}$F or $^{31}$P spectra can be integrated by program 120.

As previously mentioned, the NMR spectrum consists of a plot of intensities versus chemical shift values. A chemical shift value is a resonance frequency at which an intensity peak occurs expressed with respect to the resonance frequency of an NMR reference standard (such as tetramethysilane (TMS) or trimethylsilyl propionate (TSP)) divided by the spectrometer frequency and is usually designated in parts per million (ppm) units. Therefore, identification of a particular compound from a NMR spectrum requires knowledge of the particular pattern of intensity peaks that corresponds to that compound. Since the NMR spectrum may include intensity signals from one or more compounds of interest, the solvent used to dissolve the sample and impurities in the sample and solvent, this identification is often difficult.

Accordingly, the NMR spectrum generated by the program 120, typically as a table of intensity and chemical shift values, is provided to the compound identification and quantification program 124 as indicated schematically by arrow 126. In accordance with the principles of the invention, program 124 evaluates the data with two parallel evaluations. One of these evaluations involves identifying the qualitative presence of one or more compounds by comparing the sample NMR spectrum to a plurality of reference NMR spectra contained in a spectral database base 128 as indicated schematically by arrow 130. The other evaluation involves a quantitative evaluation of the integral proportions of the identified compounds and reporting of additional, unexplained intensity peaks using information in the compound knowledgebase 132 as schematically indicated by arrow 134.

As schematically indicated by arrow 138, compound identification and quantification program 124 generates reports 136 of the evaluation, including a basic report and a detailed report, which are stored along with data identifying the experiment. Both reports contain information on the instrument, the original spectrum and the date and time. The basic report typically contains a "pass" or "fail" result, while the detailed report contains extensive additional information regarding the results of the experiment.

Figure 2:
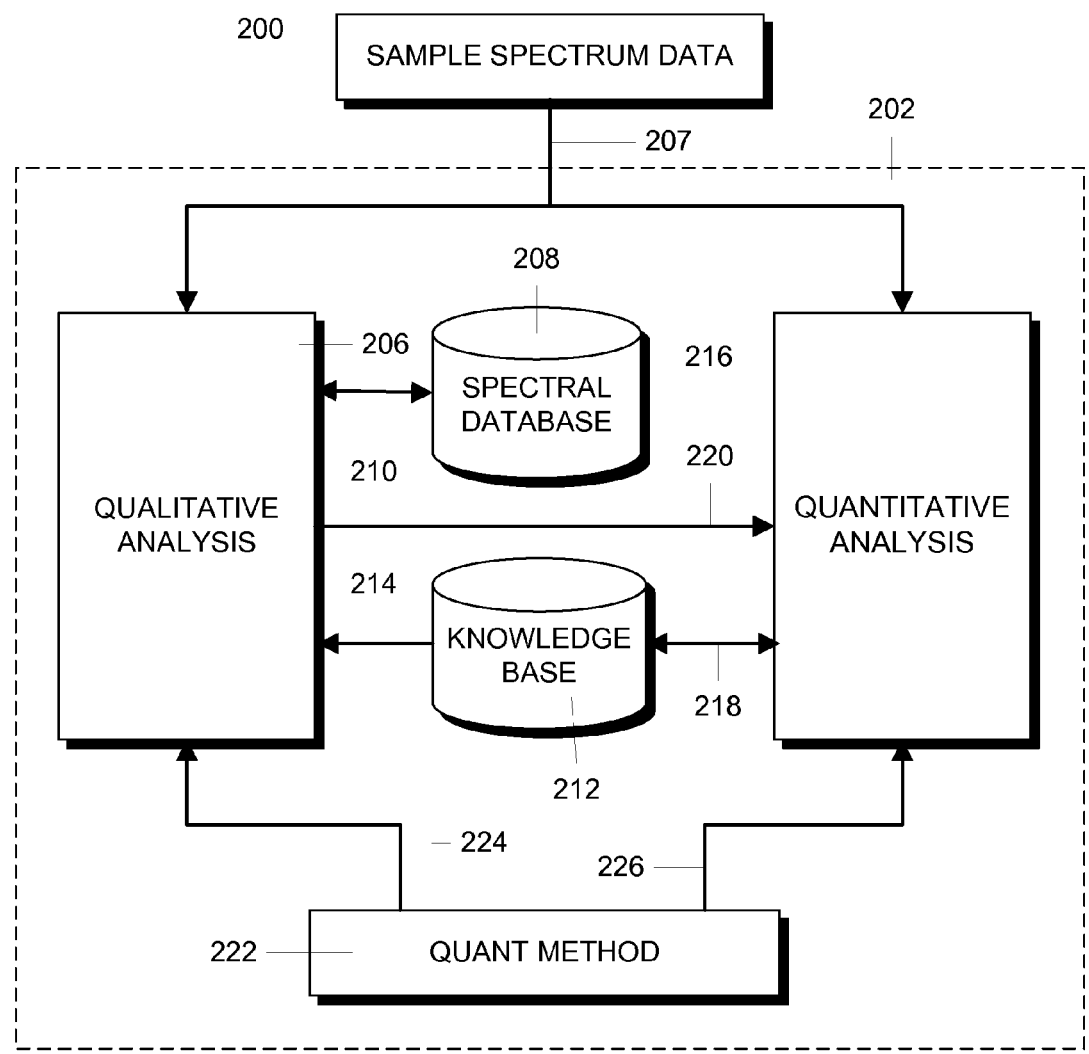
FIG. 2 is a detailed block schematic view of a compound identification and quantification system.

The operation of the compound identification and quantification program 124 is disclosed in more detail in FIG. 2. Processed data 200 from the spectrum generation program 120 is passed to the compound identification and quantification program 202 for identification and quantification of individual compounds of the sample as indicated schematically by arrow 204. Evaluation is performed by two analysis methods. The first analysis method is a qualitative analysis method 206 based on spectral matching of the spectrum 200 with reference spectra in spectral database 208 as indicated schematically by arrow 210 using information in knowledgebase 212 as indicated schematically by arrow 214. When a compound in the spectrum 200 is identified by qualitative analysis method 206, that information is forwarded to the quantitative analysis method 216 as indicated by arrow 220. Quantitative analysis method 216 confirms the identification using information in knowledgebase 212 as indicated schematically by arrow 218. In one embodiment, analysis methods 206 and 216 operate in parallel and positive identification from both of these methods gives confidence in the identification of a compound. Alternatively, analysis methods 206 and 216 may operate in tandem.

Both methods are controlled by parameters in a quantification or "quant" method 222 as indicated schematically by arrows 224 and 226 and as described in more detail below. The quant method 222 also sets the level of contaminants allowed in a passing sample and thresholds which result in a failing sample.

The inventive process uses a spectral database 208 and a knowledgebase 212. The spectral database 208 can be a standard database containing common constituents. Each facility that screens materials different from those provided with a standard spectral database will need to establish a spectral database and a knowledgebase containing compounds screened in their facility.

A spectral database, such as database 208, contains a plurality of spectrum entries. Each spectrum entry is created by examining a spectrum of a known pure reference material, assigning multiplicity and coupling patterns to peak intensity assignments and correlating them to the chemical structure of that material. Conventional software is available in order to assist with this process. For example, software which is suitable for creating and maintaining spectral databases is sold under the name AMIX® by the assignee of the present invention. Once the intensity peak assignments have been made, the AMIX software stores the information with the spectrum in the spectral database 208.

There are three spectral notations required when assigning intensity peaks in order to properly import a spectrum into the spectral database, which notations can be automatically generated from the following data:

1. One Dimensional (1D) proton spectrum data—the minimal amount of data required for proton only screening can be obtained from a 1D proton experiment. It is in this spectrum where all peak multiplicity and coupling assignments are made as described below. Peaks can also be annotated for importing atom count for quantification.
2. Two Dimensional Heteronuclear Single Quantum Coherence (2D-HSQC) spectrum data-screening for compounds containing carbon requires data from a conventional 2D-HSQC experiment. This experiment can be a standard HSQC experiment or multiplicity-edited HSQC experiment (Ed-HSQC).
3. Molecular structure file—this can be used for peak annotation, but is not absolutely necessary for annotation. The benefit when annotating in accordance with the molecular structure file is that concentration assignments reported by the quantification method will coincide with the numerical atom assignments from the structure file.

Figure 3:
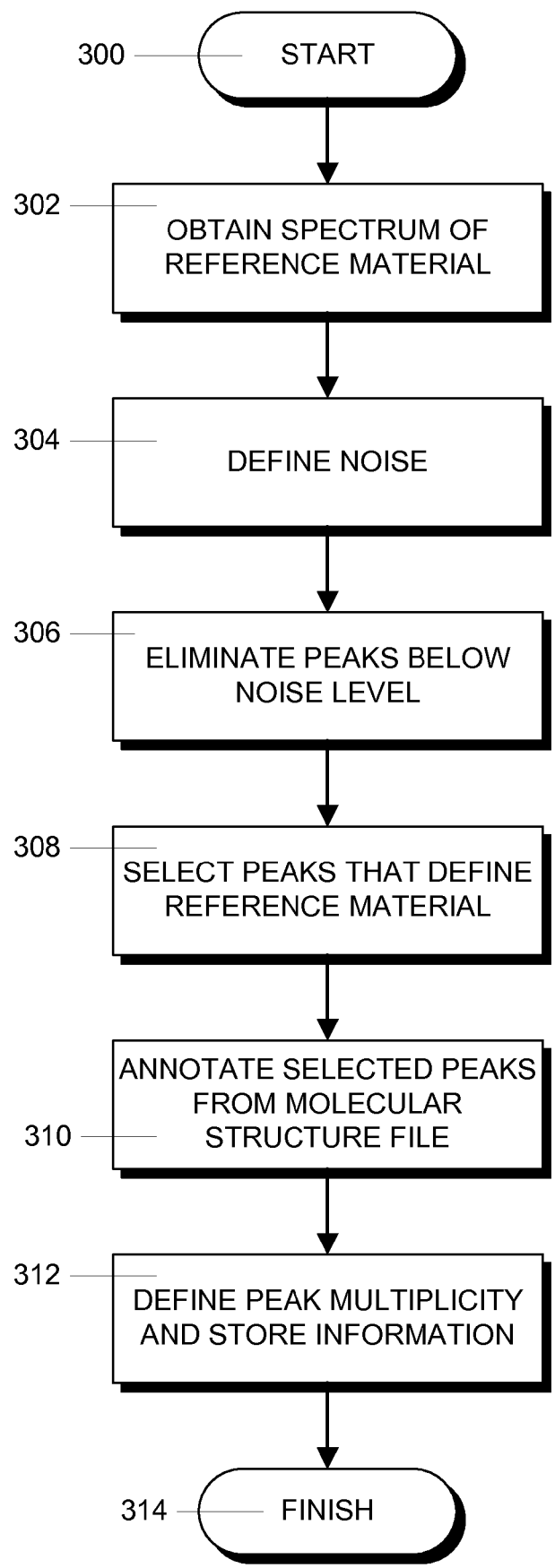
FIG. 3 is a flowchart showing the steps in an illustrative process for compiling a spectral database.

The process of creating entries in a spectral database, such as database 208, is illustrated in the flowchart shown in FIG. 3. This process begins in step 300 and proceeds to step 302 where spectral data generated by an experiment on a pure reference compound that is to be entered into the spectral database is obtained using a spectrometer and spectrum generation program as discussed above. In step 304, the data is first prepared for analysis by defining a noise level which sets a threshold intensity level above which peaks are retained and below which peaks are removed from the spectrum. In one embodiment, noise is defined by dividing the spectrum into sixteen equidistant regions, or a minimum of 512 points are used. The regions are then examined and the region best fulfilling the following criteria is then used to define noise:

The region mean and median are similar;
The region skewness is close to zero;
There are no real peaks in the region—no peaks above noise;
The region has the most Gaussian-like distribution;
Noise is then defined as the mean of this region plus a factor (F) times the standard deviation as follows:

$$\text{Noise} = \text{Avg} + (F*\text{STD})$$

Peak identification is then based on the factor F and a user-selected LOQ (Level of Quantification) and LOD (Level of Detection) for the appropriate spectral evaluation scheme. In a composite experiment, the user would define the LOQ for the $^1$H spectrum and the LOD for the $^{13}$C spectrum. For example, the user might set LOQ (STD=3.0) on the $^1$H experiment and LOD (STD=10) on the $^{13}$C experiment.

After noise has been defined, in step 306, line shape analysis is performed on the spectrum to remove all peak data below the defined noise level. Peaks that are not associated with the reference compound (e.g. water and NMR reference compounds, such as TMS or TSP) are also removed. The resulting 1D or 2D-HSQC spectrum (as described above) is then plotted and displayed in a viewer.

Intensity peaks that will define the reference material are then selected or picked in step 308. Tools for graphically assigning intensity peaks within a spectrum are found in the AMIX program and described fully in the AMIX Users Manual which is hereby incorporated by reference in its entirety. Using the AMIX program, peaks can be quickly picked with an "Auto Peak Pick" function or manually selected. The resulting picked peaks will be displayed on the plot with tick marks displayed above the peaks and the program stores the chemical shift numbers at which the peaks occur.

Next, in step 310, the selected peaks are then annotated from a conventional molecular structure file. In order to do this, both the molecular structure and the spectrum are displayed side-by-side. One or more atoms from the molecular structure are selected and the signal peak in the spectrum generated by these atoms is selected causing the AMIX program to store the correspondence between the atoms and the signal peak.

Finally, in step 312, peak multiplicity identification is performed by picking all peaks in a multiplet on the display and assigning the level of multiplicity (singlet, doublet, triplet, etc.). Once a multiplet has been indentified, the AMIX software measures the coupling constants. Once all of peaks have been picked, annotated and correctly defined by multiplicity the peak spectral data, any annotations and multiplicity information is imported into, and stored in, the spectral database. The process then ends in step 314. This process is repeated for each reference compound likely to be encountered in the laboratory for which the spectral database is being constructed.

Quantification of each compound observed in a spectrum requires a list of specific chemical shifts and the atom count in a predetermined signal region surrounding each selected peak in the spectrum. The area under the peak is then determined by an integration process over the predetermined region. The presence of a compound will be confirmed when the all of the peak signal regions possess integrals and the integrals are in proportion to their respective atom counts.

The inventive screening process utilizes an NMR knowledgebase 214 to assist with the quantification process. The knowledgebase is a collection of definitions of spectral properties of all of the compounds that are to be screened. The knowledgebase includes the following information for each compound in the spectral database 208:

| | |
|---|---|
| Name | the compound name used in the knowledgebase (the same as the name used in the spectral database); |
| Molecular weight | used in the calculation of concentration; |
| Compound regions | the areas in the NMR spectrum of the compound where a signal intensity peak is expected and the number of atoms at the peak is defined for $^1$H and $^{13}$C spectra (and $^{19}$F or $^{31}$P spectra if the sample spectra could be one of these); |
| Quantification | define the shape of the peak within each compound region, including the expected coupling pattern, the measured coupling of line splitting, and whether the peak should be used for quantification. Defined coupling patterns include singlet, doublet, triplet, quartet, quintet, septet, doublet of doublets, doublet of triplets and doublet of quartets; |
| Multiplet identification | defines tolerances on multiplet ratios (when to stop picking peaks relative to main peak in a multiplet) and J-coupling ranges. |

The knowledgebase can be initially populated with reference samples by importing the spectral data and corresponding molecular file for each reference material from the spectral database described above.

A "quant" method or quantification method 222 defines how a spectrum of a particular raw material is evaluated by specifying which compounds are expected in the raw material sample, including the main component, adulterants and impurities, which signals are irrelevant (for example, the solvent signal), and how the final report should discriminate between a sample that passes or fails the adulterant threshold requirements. The quant method 222 incorporates the definitions in the knowledgebase 212 plus some additional settings for limits on adulterant levels and is specific to a raw material. Each quant method is defined by the following user-selectable parameters:

| | |
|---|---|
| Method Name | the name of the method; |
| Compound list | a list of compounds in the knowledgebase used to set the compound definitions of known constituents. Each compound in the list is assigned a compound type selected from main component, additive, adulterant, impurity, solvent or NMR reference signal representing the likely reason for its presence in the sample; |
| Report format | specifies a 'Pass/Fail' or numerical results report and the precision of a numerical report; |
| Integrate by | selects whether the method should integrate by peak fitting or use a general region integration routine; |
| Concentration | defines the integration method that will be used; |
| Minimum reported | defines the level of integration relative to the main |

| | |
|---|---|
| threshold | component at which any signal not defined in the Compound List is reported; |
| Failure threshold | defines the level of integration relative to the main component at which any signal not defined in the Compound List is reported and produces a FAIL result in the final report; |
| Noise factor | number of standard deviations (STDs) above noise to define real peaks for any signal. |
| Spectrabase | the spectral database which is used to detect matches after quantification. It will determine if any compounds in the database which are not in the Compound List are sin the pectrum; |
| Experiment type | name of the experiment type which is defined in the spectral database; |
| Min match factor | defines the minimum level of confidence from a match at which the presence of a compound from spectral database is reported. |
| Max. shift | plus and minus values creating a search region around a spectrum peak used to determine spectral database matching; |
| Apply min. concentration | defines a minimum detectable level (used if screening by a minimum detectable level is desired). |
| Apply max. concentration | defines a maximum detectable level (used if screening by a maximum detectable level is desired). |

The qualitative analysis 206 is performed by spectral matching. Spectral matching, in turn, is performed by projecting newly-acquired spectrum data 200 onto a previously-acquired spectrum contained in spectral database 208 of a known, pure reference sample and repeating this process with different reference samples until a spectral match is obtained. For proper performance, the conditions under which the spectra are acquired, such as solvent, pulse sequence, and temperature must be identical between the reference library/knowledgebase spectra and the newly acquired spectrum. As with the reference data in database 208, the spectrum data 200 is first prepared for analysis by defining a noise level and performing lineshape analysis to remove peaks with amplitudes below the noise level and irrelevant peaks.

The spectral matching process is conducted in two parts. First, the process checks for the presence of compounds identified in compound list of the applicable quant method 222 by retrieving the spectra of these compounds from the spectral database 208. After these compounds have been checked, a second matching process is conducted, possibly using another spectral database (as specified in the Spectrabase field of the quant method), to determine if compounds that are not on the quant method compound list exist in the sample.

Figure 4A:
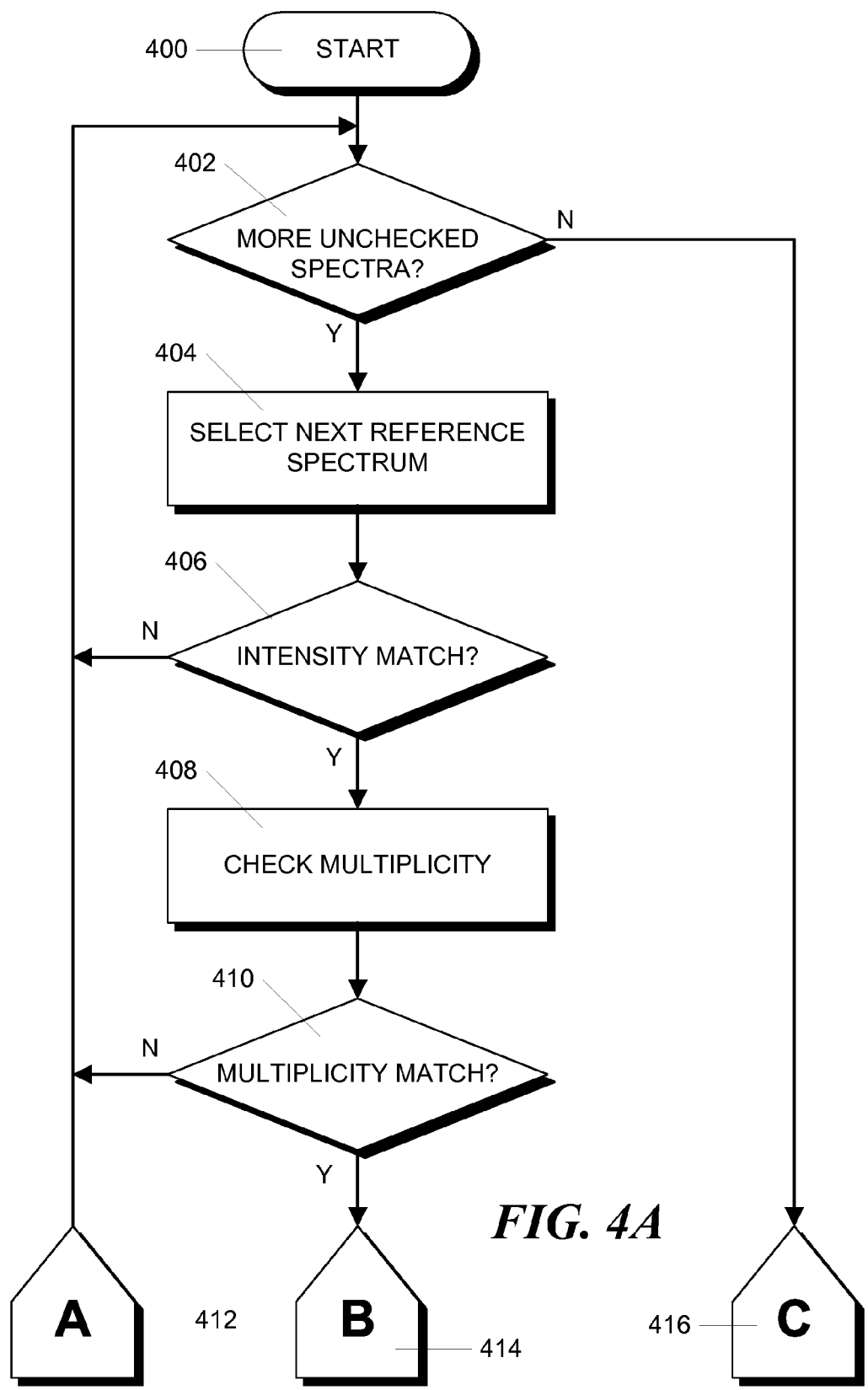
FIGS. 4A and 4B, when placed together, form a flowchart showing the steps in an illustrative program for performing a qualitative analysis by searching for compounds in the spectral database.
Figure 4B:
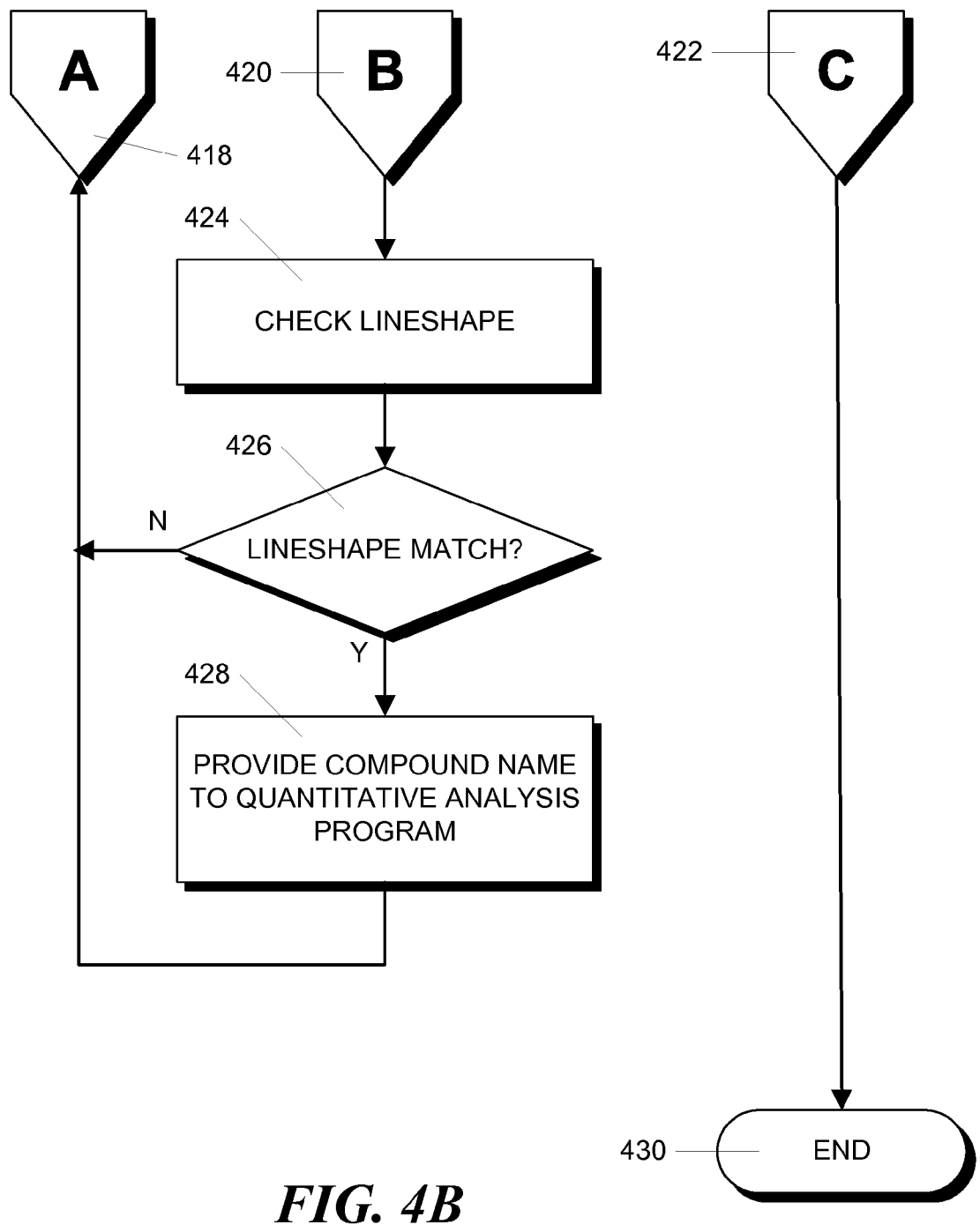

The steps in each spectral matching process are illustrated in FIGS. 4A and 4B. The process begins in step 400 and proceeds to step 402 where a determination is made whether any unchecked spectra exist either in the quant method compound list or in the spectral database 208 itself. If unchecked spectra exist, in step 404, spectral data for the next reference spectrum in the compound list or in the database 208 is retrieved (as indicated by arrow 210) and compared to the sample spectrum data 200. Additional information for the compound is also retrieved from knowledgebase 212 using the compound name as schematically indicated by arrow 214. The criteria for a spectral match are that the sample spectrum 200 and the reference spectrum must both have intensity in a search region surrounding the chemical shift value stored in the spectral database. The search region is defined in the Max. shift information in the quant method and an exemplary search region is +/−0.02 ppm. In step 406, a determination is made whether the intensities of the reference spectrum and the sample spectrum match. If not, the process returns to step 402 to determine whether additional unchecked reference spectra exist and to step 404 to select the next reference spectrum.

Alternatively, if in step 406, it is determined that an intensity match exists between the sample spectrum and the selected reference spectrum, then the process proceeds to step 408 where the multiplicity of each peak in the sample spectrum is compared to the multiplicity information stored Multiplet identification field of the compound record retrieved from knowledgebase 212. If the multiplicity does not match, the process returns to steps 402 and 404 to select another reference spectrum.

Alternatively, if the multiplicity matches, as determined in step 410, the process proceeds, via off-page connectors 414 and 420, to step 424 where a lineshape check is performed using the Quantification information in the knowledgebase record. If the lineshapes match as determined in step 426, then the compound name is provided to the quantitative analysis 216 as indicated by arrow 220 in FIG. 2 in step 428.

If the lineshapes do not match as determined in step 426, then the process returns, via off-page connectors 418 and 412 to steps 402 and 404 to select another reference spectrum. Operation continues in this manner until a match is determined in step 426 or no unchecked reference spectra exist, as determined in step 402. In this latter case, the process proceeds, via off-page connectors 416 and 422 to step 430 where the process ends.

Figure 5:
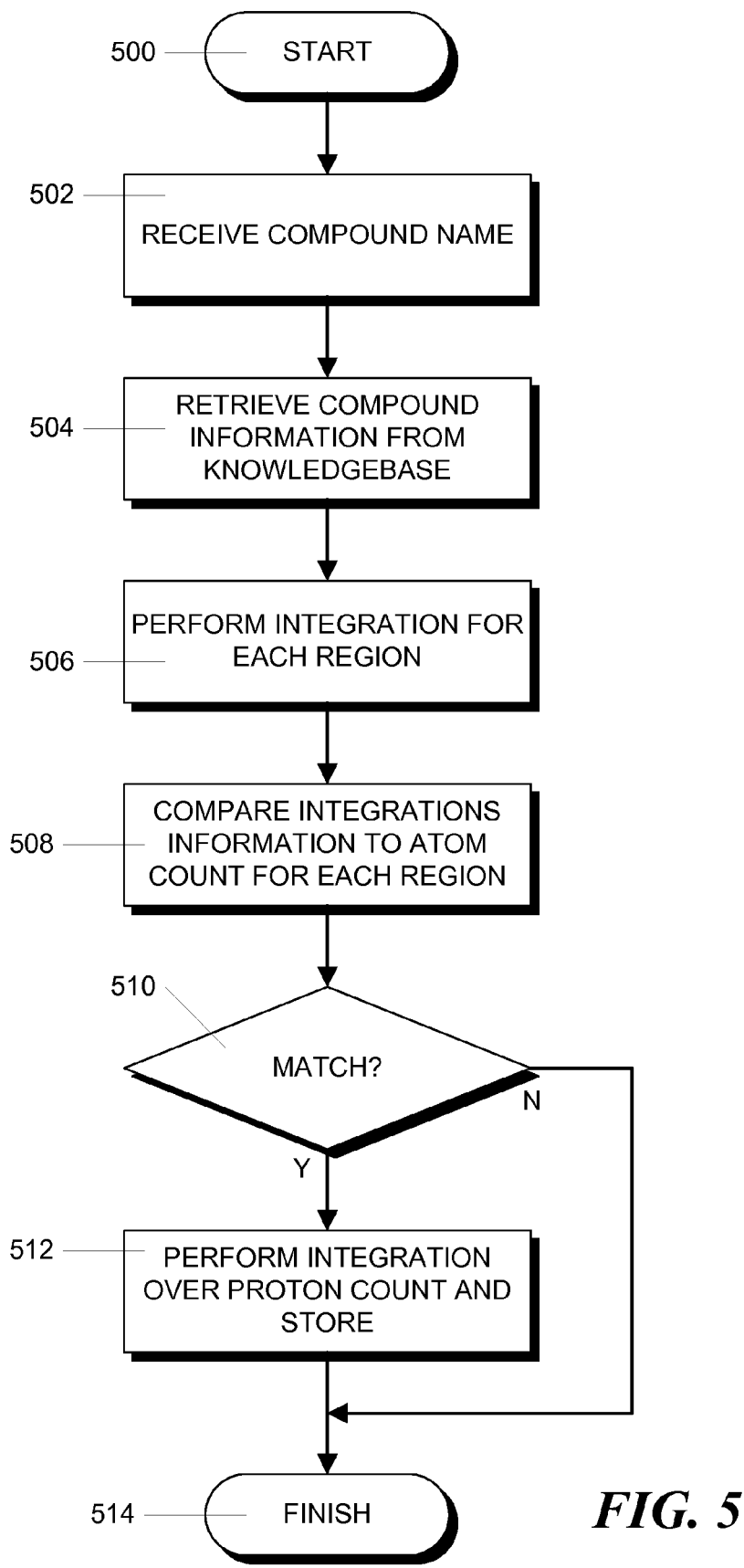
FIG. 5 is a flowchart showing the steps in an illustrative process for performing a quantitative examination of a raw material spectrum.

The quantitative analysis method is shown in FIG. 5. This method begins in step 500 and proceeds to step 502. When a compound name is received from the qualitative analysis method 206 as shown in step 502, the compound information is retrieved from the knowledgebase 212 as indicated by arrow 218. In step 506, an integration of the relative intensity of the sample spectrum 200 is performed for each compound region specified in the retrieved knowledgebase record using the integration by and concentration information specified by the quant method 222.

In step 508, the results of the integrations for each region are compared to the atom count for that region as specified by the compound region information in the retrieved knowledgebase record. If one atom is present in the region, then an integration value of one is expected. Similarly, an integration value of two correlates with two atoms, etc. If all of the integration values match the specified atom numbers as determined in step 510, then compound identification is confirmed and a final integration is performed over all protons in the compound and the integration result is stored in step 512 under the compound name. The process then finishes in step 514.

Alternatively, if in step 510 it is determined that no match is detected, then the process simply finishes in step 514.

At the end of the entire process, integration values will have been stored for all compounds identified in the sample, including the main component, the adulterants, impurities and other compounds. After eliminating those values that are less than the minimum reported threshold specified in the quant method, ratios can then be formed of these values and compared to the failure threshold and concentration thresholds specified in the quant method in order to determine the result of the analysis.

In order to insure that the spectrometer 102 remains properly calibrated, system suitability tests may be performed either on a periodic basis or if the shim test fails as described above. System Suitability Tests consist of four experiments: lineshape, $^1$H sensitivity, $^{13}$C sensitivity and temperature. The results of each test must "pass'" before the spectrometer is deemed to be operating properly and raw material samples can be analyzed.

The $^1$H lineshape test, which is also referred to as the "humptest" automatically measures and determines the $^1$H lineshape using a GLP $^1$H lineshape standard sample of 1% chloroform in acetone. The width of the chloroform line at 0.55% height and 0.11% height is calculated with a double exponential fit along the left and right side of the signal. The resolution test is also performed and evaluates the width of the chloroform signal at half height. These values are compared with specifications set by the user. The test is passed if the results are better than the defined values.

The $^1$H sensitivity test automatically measures and determines the $^1$H sensitivity. While this test can be performed with almost any sample, the typical sample is 0.1% ethylbenzene in chloroform-d. The height of the biggest signal between user-specified signal limits is calculated. A noise window of width Noise delta in ppm is shifted in 25 steps along the spectrum between the specified noise limits. Each time, the noise value is determined and the signal-to-noise (S/N) ratio is calculated with respect to the height of the biggest signal within the signal limits. The best value must meet a user-defined specification.

The $^{13}$C sensitivity test automatically measures and determines the $^{13}$C sensitivity. While this test can also be performed with almost any sample, the typical is 10% ethylbenzene in cholorform-d. The height of the biggest signal between user-defined signal limits is calculated. A noise window of Noise delta ppm is shifted in 25 steps along the spectrum between the specified noise limits. Each time, the noise value is determined and the signal-to-noise ratio is calculated with respect to the height of the biggest signal. The best value must meet a user-defined specification.

The temperature test automatically measures and, if necessary, adjusts the temperature to a user-defined requested temperature. The experiment is designed to run after the first three suitability tests. In one embodiment, the requested temperature is set with a 99.8% methanol-d4 temperature calibration standard which has a linear range from 282° K. to 330° K. The test will attempt to adjust the temperature to the set point five times before failing. The final observed temperature after adjustment is recorded in status parameters.

The system is designed to adjust to shim changes over the lifetime of the spectrometer. This is done by updating and using a default shim file that is used for all samples including the system suitability test samples. Once a $^1$H lineshape suitability test has been completed successfully as discussed above, the shim set is written to storage for a particular probe. If a default shim set does not exist for the probe, then the current shims are used.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. An automated raw material screening device that performs a measurement on a sample with an NMR spectrometer and processes resulting signals to generate a sample NMR spectrum of the sample, the device comprising:
    a qualitative analysis unit that identifies at least one reference NMR spectrum corresponding a compound present in the sample; and
    a quantitative analysis unit that integrates relative signal intensity signals of the sample spectrum in regions of peak intensity in the one reference NMR spectrum and compares integration results to a number of atoms in each region in order to confirm identification of the compound.

2. The device of claim 1 wherein the qualitative analysis unit compares the sample spectrum to a plurality of reference NMR spectra stored in a spectral database.

3. The device of claim 2 wherein the qualitative analysis unit identifies the one reference NMR spectrum by selecting a reference NMR spectrum that has intensity peaks at chemical shift locations at which the sample NMR spectrum has intensity peaks.

4. The device of claim 3 wherein the qualitative analysis unit identifies the one reference NMR spectrum by performing a lineshape analysis and a multiplicity analysis on intensity peaks of the sample NMR spectrum that correspond to intensity peaks of the selected reference NMR spectrum.

5. The device of claim 4 wherein the lineshape analysis and the multiplicity analysis use information stored in a compound knowledgebase.

6. The device of claim 1 wherein the qualitative analysis unit and the quantitative analysis unit are controlled by a set of parameters that is predetermined for the sample.

7. The device of claim 6 wherein the predetermined parameters include information identifying reference NMR spectra corresponding to a main component, adulterants, impurities and other compounds likely to be found in the sample.

8. The device of claim 7 wherein the quantitative analysis unit integrates signal intensity signals of the sample spectrum using an integration method specified in the predetermined parameters.

9. The device of claim 1 wherein the quantitative analysis unit integrates intensity signals of the sample spectrum in regions surrounding intensity peaks in each reference NMR spectrum for all protons in the reference NMR spectrum in order to determine a quantities of compounds present in the sample.

10. The device of claim 1 wherein the quantitative analysis unit integrates intensity signals of the sample spectrum in regions surrounding intensity peaks in each reference NMR spectrum for all nuclei in the reference NMR spectrum in order to determine a quantities of compounds present in the sample.

11. The device of claim 1 further comprising a test unit that performs a series of system suitability tests in order to assure that the NMR spectrometer is performing to predetermined specifications.

12. The device of claim 11 wherein the system suitability tests comprise a $^1$H lineshape test, a $^1$H sensitivity test, a $^{13}$C sensitivity test and a temperature test.

13. The device of claim 11 wherein the system suitability tests are performed periodically.

14. The device of claim 11 wherein the system suitability tests are performed whenever a problem is detected in the device.

15. A method for screening raw materials by performing a measurement on a sample with an NMR spectrometer and processing resulting signals to generate a sample NMR spectrum of the sample, the method comprising:
    (a) identifying at least one reference NMR spectrum corresponding a compound present in the sample; and
    (b) integrating relative signal intensity signals of the sample spectrum in regions of peak intensity in the one reference NMR spectrum and comparing integration results to a number of atoms in each region in order to confirm identification of the compound.

16. The method of claim 15 wherein step (a) comprises comparing the sample spectrum to a plurality of reference NMR spectra stored in a spectral database.

17. The method of claim 16 wherein step (a) further comprises selecting from the plurality of reference NMR spectra a reference NMR spectrum that has intensity peaks at chemical shift locations at which the sample NMR spectrum has intensity peaks.

18. The method of claim 17 wherein step (a) further comprises performing a lineshape analysis and a multiplicity analysis on intensity peaks of the sample NMR spectrum that correspond to intensity peaks of the selected reference NMR spectrum.

19. The method of claim 18 wherein the lineshape analysis and the multiplicity analysis use information stored in a compound knowledgebase.

20. The method of claim 15 wherein step (a) and step (b) are performed in accordance with a set of parameters that is predetermined for the sample.

21. The method of claim 20 wherein the predetermined parameters include information identifying reference NMR spectra corresponding to a main component, adulterants, impurities and other compounds likely to be found in the sample.

22. The method of claim 21 wherein step (b) comprises integrating signal intensity signals of the sample spectrum using an integration method specified in the predetermined parameters.

23. The method of claim 15 wherein step (b) comprises integrating intensity signals of the sample spectrum in regions of peak intensity in each reference NMR spectrum for all protons in the reference NMR spectrum in order to determine a quantities of compounds present in the sample.

24. The method of claim 15 wherein step (b) comprises integrating intensity signals of the sample spectrum in regions of peak intensity in each reference NMR spectrum for all nuclei in the reference NMR spectrum in order to determine a quantities of compounds present in the sample.

25. The method of claim 15 further comprising performing a series of system suitability tests in order to assure that the NMR spectrometer is performing to predetermined specifications.

26. The method of claim 25 wherein the system suitability tests comprise a $^1H$ lineshape test, a $^1H$ sensitivity test, a $^{13}C$ sensitivity test and a temperature test.

27. The method of claim 25 wherein the system suitability tests are performed periodically.

28. The method of claim 25 wherein the system suitability tests are performed whenever a problem is detected.

* * * * *